US00PP23013P2

(12) United States Plant Patent
Bergman

(10) Patent No.: US PP23,013 P2
(45) Date of Patent: Sep. 4, 2012

(54) ***CHRYSANTHEMUM* PLANT NAMED 'CIDZ0017'**

(50) Latin Name: *Chrysanthemum×morifolium*
Varietal Denomination: CIDZ0017

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/136,551

(22) Filed: Aug. 4, 2011

(51) Int. Cl.
*A01H 5/00* (2006.01)

(52) U.S. Cl. ..... Plt./294

(58) Field of Classification Search ..... Plt./294
See application file for complete search history.

*Primary Examiner* — Kent L Bell
(74) *Attorney, Agent, or Firm* — Joshua L. Price

(57) ABSTRACT

A new *Chrysanthemum* plant named 'CIDZ0017' particularly distinguished by the small daisy-type inflorescences, white ray floret color, small medium green foliage, very compact growth habit and is very freely branched.

1 Drawing Sheet

Latin name of the genus and species of the plant claimed: *Chrysanthemum×morifolium.*

Varietal denomination: 'CIDZ0017'.

BACKGROUND OF THE NEW PLANT

The present invention comprises a new *Chrysanthemum*, botanically known as *Chrysanthemum×morifolium*, and hereinafter referred to by the variety name 'CIDZ0017'.

'CIDZ0017' is a product of a planned breeding program. The new cultivar has small daisy-type inflorescences, white ray floret color, small medium green foliage, very compact growth habit and is very freely branched.

'CIDZ0017' originated from a hybridization made in February 2004 in a controlled breeding environment in Salinas, Calif. The female parent was the proprietary plant designated 'YB-A7754', unpatented, with white inflorescences, a faster flowering response time and flowers more uniformly.

The male parent of 'CIDZ0017' was an unpatented, proprietary plant identified as 'YB-A7224' with white inflorescences, produces pollen and the disc florets have more green. The resultant seed was sown in July 2004 in Fort Myers, Fla., USA.

'CIDZ0017' was selected as one flowering plant within the progeny of the stated cross in November 2004 in a controlled environment in Fort Myers, Fla., USA.

The first act of asexual reproduction of 'CIDZ0017' was accomplished when vegetative cuttings were propagated from the initial selection in February 2005 in a controlled environment in Fort Myers, Fla., USA.

BRIEF SUMMARY OF INVENTION

Horticultural examination of plants grown from cuttings of the plant initiated in December 2004, and continuing thereafter, has demonstrated that the combination of characteristics as herein disclosed for 'CIDZ0017' are firmly fixed and are retained through successive generations of asexual reproduction.

'CIDZ0017' has not been observed under all possible environmental conditions. The phenotype may vary significantly with variations in environment such as temperature, light intensity and day length.

A Plant Breeder's Right for this cultivar was applied for in Canada on August 17, 2010 (10-7075). 'CIDZ0017' has not been made publicly available more than -one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical inflorescence and foliage characteristics of 'CIDZ0017' with colors being as true as possible with an illustration of this type. The photographic drawing shows three flowering potted plants of the new variety, and a close-up of the inflorescence.

DETAILED BOTANICAL DESCRIPTION

The plant descriptions, measurements, and aforementioned photographs were taken in Gilroy, Calif. in early May 2011 under natural light. These plants were propagated and grown in Nipomo, Calif. and shipped to Gilroy, Calif. for the data collection and photographs. These plants were approximately 11 weeks of age; grown as four plants together in a six inch pot under greenhouse trial conditions Color references are made to The Royal Horticultural Society Colour Chart (R.H.S.) 2001.

TABLE 1

DIFFERENCES BETWEEN THE NEW VARIETY 'CIDZ0017' AND A SIMILAR VARIETY

| | 'CIDZ0017' | 'White Yomistique' (U.S. Plant Pat. No. 21,421) |
|---|---|---|
| Flower color: | Whiter | Not as white |
| Timing of flowering: | More uniform, more at the same time | Less uniformly |

Plant:
*Form, growth and habit*.—Herbaceous fleurette pot type, stems upright, freely branching.
*Plant height*.—Approximately 13.0 cm.
*Plant height* (*inflorescence included*)(*cm*).—17-18.0 cm.
*Plant width* (*cm*).—17-19.0 cm.
*Garden performance and tolerance to weather*.—Very good.
*Crop time to flowering*.—About 10 weeks.

Roots:
*Number of days to initiate roots*.—About 4 days at about 22 degrees C.
*Number of days to produce a rooted cutting*.—About 9-11 days at 22 degrees C.
*Type*.—Fine, fibrous, free branching.
*Color*.—RHS N155B but whiter.

Foliage:
*Arrangement*.—Alternate, simple.
*Immature, leaf color, upper surface*.—RHS 137A.
*Lower surface*.—RHS 137C but appears lighter due to hairs.
*Mature, leaf color, upper surface*.—Between RHS 137A and RHS 137B.
*Lower surface*.—RHS 137C but appears lighter due to hairs.
*Length*.—3.9-4.4 cm.
*Width*.—2.9-3.0 cm.
*Shape*.—Elliptical.
*Base shape*.—Attenuate.
*Apex shape*.—Slightly mucronulate.
*Margin*.—Barely serrate; but palmately lobed; irregularly and slightly serrate.
*Texture, upper surface*.—Bifid T-shaped hairs.
*Lower surface*.—Bifid T-shaped hairs.
*Color of veins, upper surface*.—RHS 144B.
*Color of veins, lower surface*.—RHS 144B.
*Petiole color*.—RHS 144B.
*Length*.—1.4-2.1 cm.
*Diameter*.—0.25 cm.
*Texture*.—Bifid T-shaped hairs.

Stem:
*Quantity of main branches per plant*.—5-6.
*Color of stem*.—RHS 143B but appears lighter due to hairs.
*Length of stem*.—10-11.0 cm.
*Diameter*.—0.3-0.4 cm.
*Length of internodes*.—0.5-1.3 cm.
*Texture*.—Bifid T-shaped hairs.
*Color of peduncle*.—RHS 143B but appears lighter due to hairs.
*Length of peduncle*.—3.-4.0 cm.
*Peduncle diameter*.—0.2 cm.
*Texture*.—Bifid T-shaped hairs.

Inflorescence:
*Type*.—Compositae type, solitary inflorescences borne terminally above foliage, ray florets arranged acropetally on a capitulum.
*Quantity of short days to flowering* (*response time*).—Approximately 6 weeks.
*Quantity of inflorescences per plant*.—Approximately 40.
*Lastingness of individual blooms on the plant*.—About 4 weeks.
*Fragrance*.—Slightly spicy.

Bud (just before opening/showing color):
*Color*.—RHS 155B but whiter.
*Length* (*cm*).—0.5-0.6 cm.
*Width* (*cm*).—0.6-0.7 cm.
*Shape*.—Oblate.

Immature inflorescence:
*Diameter*.—2.3-2.5 cm.
*Color of ray florets, upper surface*.—RHS 155B but whiter.
*Lower surface*.—RHS 155B but whiter.

Mature inflorescence:
*Diameter*.—3.1-3.2 cm.
*Depth*.—0.6-0.7 cm.
*Total diameter of 'disc'*.—1.1-1.2 cm.
*Receptacle height*.—0.3 cm.
*Receptacle diameter*.—0.4 cm.

Ray florets:
*Average quantity of florets*.—40-55 in 2-3 whorls.
*Color of florets, upper surface*.—RHS 155B but whiter.
*Lower surface*.—RHS 155B but whiter.
*Length*.—1.3-1.5 cm.
*Width*.—0.4-0.5 cm.
*Shape*.—Elliptical.
*Apex shape*.—Irregularly emarginate.
*Margin*.—Entire.
*Texture, upper surface*.—Papillose.
*Lower surface*.—Papillose.

Disc florets:
*Average quantity of florets*.—Approximately 150.
*Color of florets*.—Immature, closest to RHS 1B with RHS 143B to RHS 143C apex, that quickly matures to about RHS 3A to RHS 3B apex and RHS 1C basally.
*Length*.—0.3-0.4 cm.
*Width*.—0.1 cm.
*Shape*.—Tubular, elongated.
*Apex shape*.—Acute, 5 pointed.

Phyllaries:
*Quantity*.—Approximately 25.
*Color, upper surface*.—RHS 138A.
*Lower surface*.—RHS 138A but appears lighter due to hairs.
*Length*.—0.4-0.5 cm.
*Width*.—0.15-0.2 cm.
*Shape*.—Lanceolate.
*Apex shape*.—Obtuse.
*Base*.—Fused.
*Margins*.—Entire; papery.
*Texture, upper surface*.—Glabrous.
*Lower surface*.—Bifid T-shaped hairs.

Reproductive organs:
*Pistil*.—1.
*Found on both florets*.—Yes.
*Length*.—0.4 cm.
*Style color*.—RHS 1C.
*Style length*.—0.3 cm.
*Stigma color*.—RHS 6A.
*Stigma shape*.—Bi-parted.
*Ovary color*.—Not observed.
*Stamens*.—4.
*Found on only disc florets*.—Yes.
*Color of filaments*.—RHS 1C but a little greener.
*Length filaments*.—0.2 cm.
*Anther color*.—RHS 8C.
*Anther length*.—0.1 cm.
*Anther shape*.—Oblong.

*Pollen amount*.—None observed.

*Color of pollen*.—N/A.

*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'CIDZ0017' substantially as illustrated and described herein.

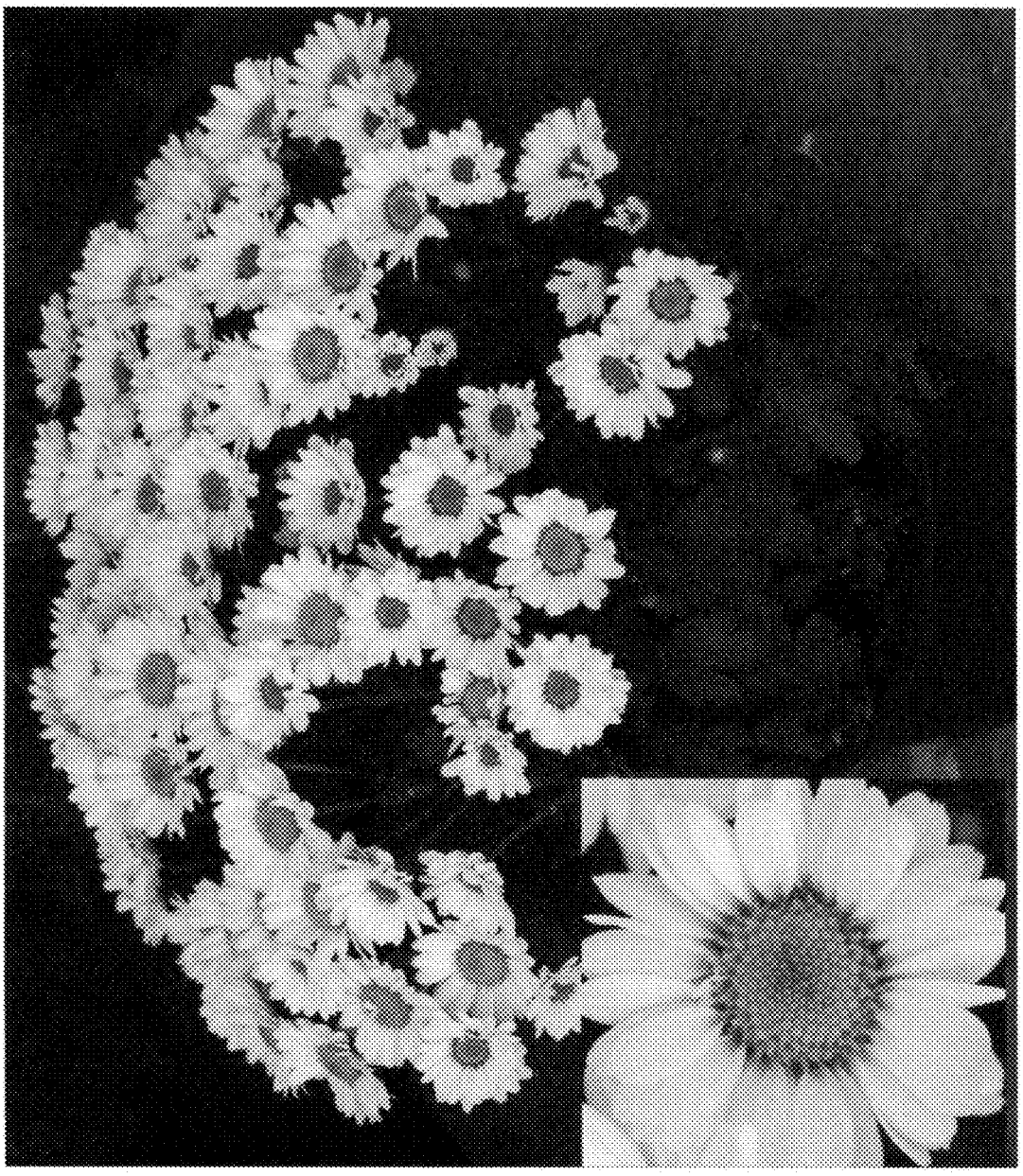

* * * * *